United States Patent [19]
Suszynski et al.

[11] Patent Number: 4,993,424
[45] Date of Patent: Feb. 19, 1991

[54] INFRARED MEDICAL THERMOMETER

[75] Inventors: Edward D. Suszynski, Vista; Ian F. Ayton, Palos Verdes Estates; James P. Stewart, Escondido; Marco A. Schilling, Lakeside; Thomas K. Gregory, Carlsbad, all of Calif.

[73] Assignee: Diatek, Incorporated, San Diego, Calif.

[21] Appl. No.: 445,438

[22] Filed: Dec. 4, 1989

[51] Int. Cl.⁵ .................. A61B 5/00; G01K 1/08
[52] U.S. Cl. ............................ 128/736; 128/634; 374/158; 374/209
[58] Field of Search .......... 128/736, 632, 633, 634; 206/306; 374/120, 121, 129, 158, 208, 209; 604/192, 194

[56] References Cited

U.S. PATENT DOCUMENTS

| | | | |
|---|---|---|---|
| 3,703,892 | 11/1972 | Meyers | 374/158 |
| 3,765,779 | 3/1973 | Hunt et al. | 374/129 |
| 3,924,469 | 12/1975 | Brandli et al. | 374/129 |
| 4,588,307 | 5/1986 | Palti | 128/736 |
| 4,602,642 | 7/1986 | O'Hara et al. | 128/736 |
| 4,797,840 | 1/1989 | Fraden | 128/736 |
| 4,863,281 | 9/1989 | Suszynski | 374/158 |

FOREIGN PATENT DOCUMENTS

0023675 5/1971 Japan .................. 374/158

Primary Examiner—Max Hindenburg
Assistant Examiner—Robin R. Longo
Attorney, Agent, or Firm—Pretty, Schroeder, Brueggemann & Clark

[57] ABSTRACT

A self-contained handheld infrared medical thermometer having an elongated probe that is reciprocably movable between a retracted position, located fully within the thermometer housing, and an extended position, located exterior to the housing. When extended, the probe is adapted for insertion into a patient's outer ear canal to measure the patient's body temperature. When the probe is retracted within the housing, a reference plate is pivoted in front of the probe, to facilitate calibration. Advancement of the probe to its extended, operative position automatically pivots the reference plate away from the advancing probe and, in addition, automatically advances a disposable protective cover from a container for a large number of such covers into a position where it automatically stretches over the advancing probe to provide hygienic protection.

32 Claims, 4 Drawing Sheets fig. 1.

INFRARED MEDICAL THERMOMETER

BACKGROUND OF THE INVENTION

This invention relates generally to medical thermometers and, more particularly, to infrared medical thermometers having elongated probes adapted for placement into a patient's ear canal.

Infrared medical thermometers of this particular kind are becoming increasingly popular for clinical use because of their high accuracy and the great speed with which temperature measurements can be obtained. Accurate temperature measurements typically can be obtained within several seconds, as contrasted with the several minutes required when using conventional glass thermometers. In addition, since the thermometer's probe is inserted only into the patient's outer ear canal, the patient experiences only minimal inconvenience.

Infrared medical thermometers of this kind typically include a hand-held unit with an elongated probe having an infrared sensor within the probe or at its base. The hand-held unit is typically placed into a mating base unit after each measurement has been made, such that the probe is located adjacent to a calibration reference surface having a particular temperature. The patient's temperature is determined based on a detected change in the signal generated by the infrared sensor when the probe is moved from the reference surface in the base unit to the patient's ear.

Although the infrared thermometer described briefly above has generally proven to be effective in providing accurate patient measurements, it is believed that the need for a separate base unit makes the apparatus unduly bulky and cumbersome to use. In addition, the need for a separate base unit restricts the thermometer's mobility. Another drawback is that the elongated probe, which is always extended from the hand-held unit, is susceptible to damage during handling, particularly when placing the hand-held unit into the base unit. There is therefore a need for an improved infrared medical thermometer that functions without the need for a separate base unit and that minimizes the possibility of damage to the probe. The present invention fulfills this need.

Infrared medical thermometers of this particular kind are generally intended for use with multiple patients, so it is desirable to place a disposable hygienic protective cover over the probe prior to use with each patient. The use of such protective probe covers can be both time consuming and inconvenient. There is therefore a need for a thermometer apparatus that automatically places such protective covers over the probe prior to each use and that automatically removes and discards the cover after use. Ideally, the apparatus should place and remove the probe covers automatically, without the need to manually position the cover relative to the probe. The present invention satisfies the need for such an automatic apparatus.

SUMMARY OF THE INVENTION

The present invention is embodied in an improved infrared medical thermometer apparatus that functions conveniently to measure patient temperatures without the need for a separate calibration unit and that automatically places and removes a protective cover over its probe each time it is used. The thermometer apparatus includes a housing adapted to be held in a user's hand and an elongated probe adapted to be inserted into a patient's ear canal to collect infrared radiation and provide a signal indicating the patient's body temperature. In accordance with the invention, the apparatus further includes extension/retraction means for selectively extending the elongated probe to an operative position outside the housing when a patient's temperature is to be measured and for selectively retracting the probe to an inoperative position fully within the housing when the measurement has been completed. The probe is therefore protected from damage due to handling after each measurement has been made.

More particularly, the thermometer apparatus is self calibrating, without the need for a separate calibration unit, by including reference means located within the housing and movable between an operative position directly in front of the elongated probe, when the probe is retracted fully within the housing, and an inoperative position alongside the probe, when the probe is extended outside the housing. The extension/retraction means includes means for selectively moving the reference means between its operative and inoperative positions. The reference means preferably includes a plate that can be selectively positioned directly in front of the elongated probe, an arm secured to the plate, and a pin and cooperating slot carried by the arm and by the housing, for guiding the plate and arm between the reference means' operative and inoperative positions. This preferably occurs simultaneous to the respective retraction and extension of the elongated probe.

In another feature of the invention, probe cover means are provided for positioning a protective cover in alignment with the probe while the probe is retracted within the housing, such that when the extension/retraction means selectively extends the probe to its operative position, the protective cover automatically covers the probe. In addition, selectable actuator means is provided for substantially simultaneously performing the three functions of (1) conditioning the reference means to move to its inoperative position, (2) conditioning the probe cover means to position a protective cover in alignment with the elongated probe, and (3) conditioning the extension/retraction means to extend the elongated probe to its operative position and, in so doing, place the protective cover over the probe. The selectable actuator means also preferably performs the substantially simultaneously functions of (1) conditioning the extension/retraction means to retract the probe to its inoperative position and, in so doing, eject the previously-used protective cover from the probe, (2) conditioning the probe cover means to engage a further protective cover, and (3) conditioning the reference means to move to its operative position directly in front of the retracted elongated probe.

In another, more detailed feature of the invention, the apparatus further includes a container for carrying a plurality of substantially identical protective probe covers, connected together end-to-end to form an elongated chain, and a pawl is provided for engaging the end-most protective cover and advancing it into alignment with the elongated probe. Each adjacent pair of protective covers is connected together by a narrow strip aligned with the centers of the covers, and the pawl includes a U-shaped end adapted to engage the rearward edge of the end-most cover, on opposite sides the narrow strip, and thereby to urge the end-most cover into alignment with the probe.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

With reference now to the drawings, and particularly to FIGS. 1–5, there is shown a handheld infrared medical thermometer having a generally pistol-shaped housing 11, a display 13, and an elongated probe 15 adapted for insertion into a patient's outer ear canal, to measure the patient's body temperature. An infrared sensor located within the probe receives infrared radiation transmitted from the ear canal and generates a corresponding electrical signal that is appropriately processed to determine the patient's body temperature. The processing is performed by appropriate electronic circuitry on printed circuit boards (not shown in the drawings) located within the thermometer housing, and the computed body temperature is displayed on the display. Electrical power for the thermometer is provided by batteries 18 located within a handle portion 19 of the housing.

The patient's body temperature is determined by comparing the infrared sensor signal generated while the sensor receives infrared radiation from the patient's ear canal with the signal generated when receiving infrared radiation from a calibration reference having a known temperature. In the past, the calibration reference was provided by a separate calibration unit into which the handheld unit was placed prior to its use with each patient. The temperature of the calibration reference located within the calibration unit was measured and, in some cases, regulated to a selected value.

In accordance with the invention, the calibration reference is provided not by a separate calibration unit, but rather by a built-in calibration plate 21 located within the handheld thermometer, itself. In particular, the elongated probe 15 is adapted to be selectively retracted into the housing 11 along the probe's longitudinal axis 23. An opening 25 is provided at the housing's front end to facilitate this retraction. As the retracted position (shown in FIG. 3) is reached, the calibration plate is moved directly in front of the probe so that the infrared sensor located within the probe receives infrared radiation substantially only from that plate. When the patient's body temperature is to be measured, the calibration plate is pivoted away from the probe and the probe extended outwardly from the housing to the position depicted in FIGS. 1 and 5, for insertion into the patient's ear.

Figure 3:
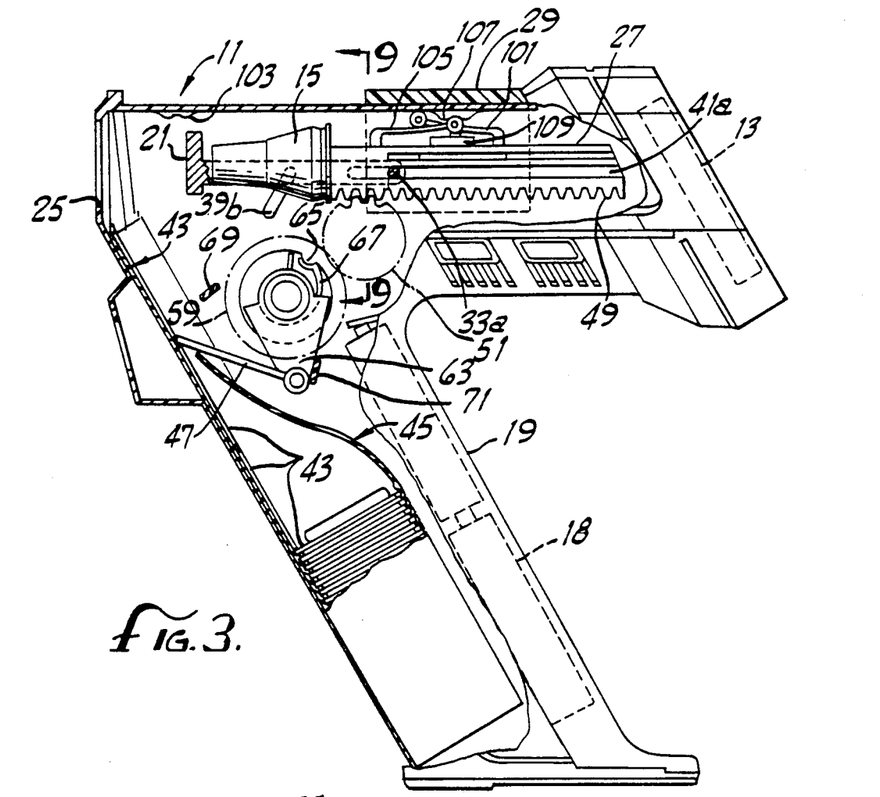
FIG. 3 is a side sectional view of the thermometer, shown with the probe in its fully retracted, inoperative position, with the calibration reference positioned directly in front of the probe, and with the pawl positioned to engage the end-most protective probe cover.
Figure 5:
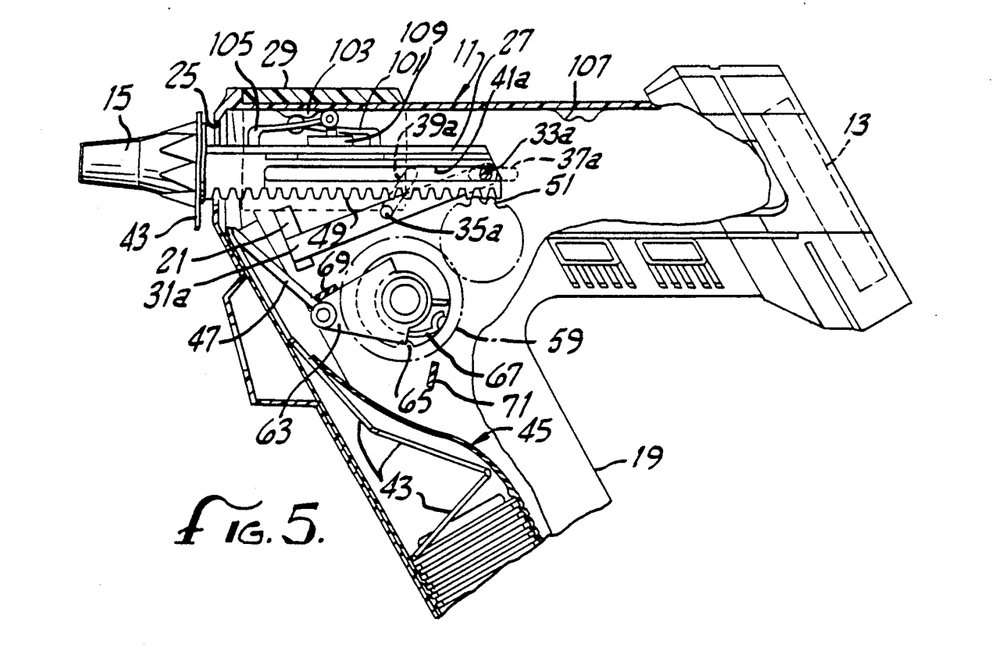
FIG. 5 is a side sectional view similar to FIGS. 3 and 4, but showing the probe advanced to its fully extended position, with the protective cover stretched over the probe.
Figure 6:
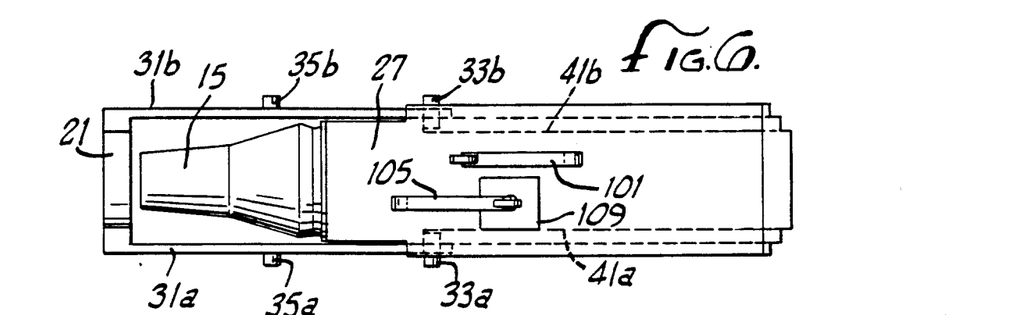
FIG. 6 is a fragmentary top view of the elongated probe and probe body, with the calibration reference positioned directly in front of it.
Figure 7:
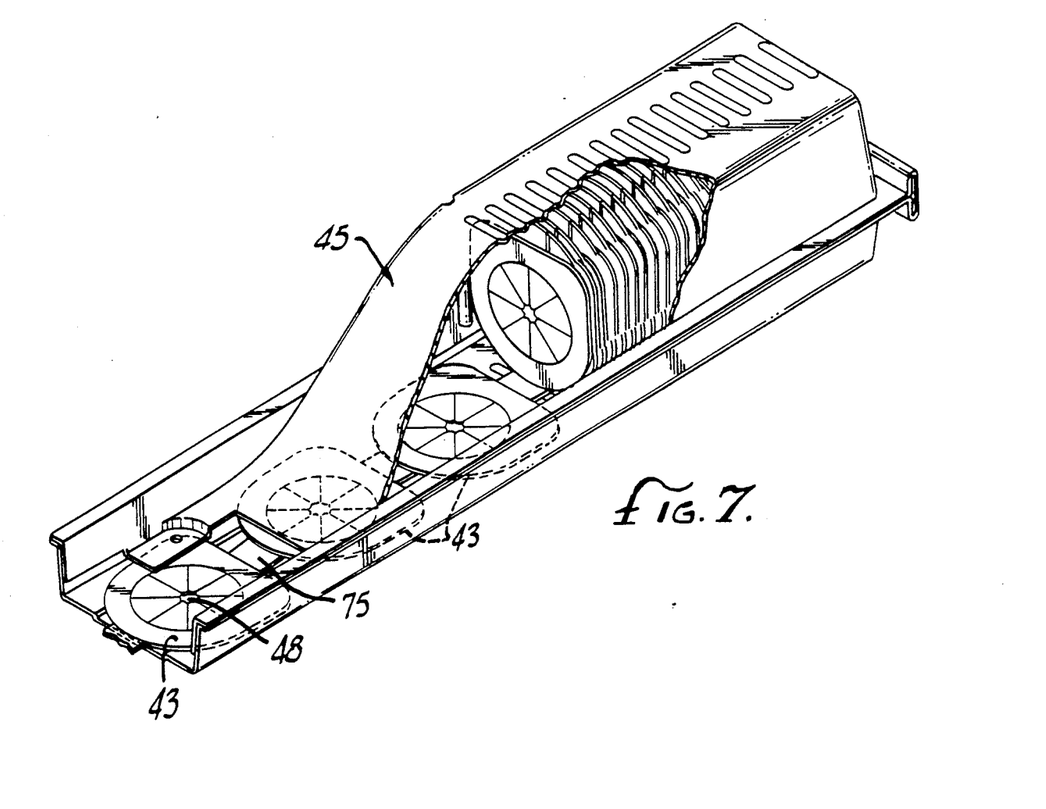
FIG. 7 is a perspective view of a container for a large number of protective probe covers of the kind that can be carried in the handle portion of the thermometer of FIG. 1.

The mechanism for extending and retracting the elongated probe will now be described with reference to the sequential views of FIGS. 3–5 and to FIG. 6. In particular, with reference initially to FIG. 3, the elongated probe 15 is located at the forward end of a sensor body 27 that is mounted for reciprocable sliding movement within the housing 11. Operatively connected to the sensor body is an indexing handle 29 that is mounted on the housing's top surface. This indexing handle is reciprocably movable toward and away from the thermometer's front end. Its forward position is depicted in FIG. 5 and its rearward position is depicted in FIG. 3. Concave finger depressions, one of which is identified by the reference numeral 30, are formed in the indexing handle's exposed surface, to facilitate its manual gripping.

The calibration plate 21 is associated with two integral support legs 31a, 31b projecting in the same direction from opposite sides of the plate. The plate and leg combination thus is generally U-shaped, as best observed in FIG. 6. When the elongated probe 15 is fully retracted within the housing 11, to the position depicted in FIGS. 3 and 6, the calibration plate is pivoted to a position directly in front of the probe, and the two legs straddle the probe and slidable sensor body 27. Manually advancing the indexing handle 29 to the intermediate position of FIG. 4 allows a spring (not shown) to pivot the calibration plate downwardly from the probe axis 23, to allow room for the advancing probe.

The pivoting movement of the calibration plate 21 and legs 31a, 31b is controlled by pins 33a, 33b and 35a, 35b projecting transversely from the legs and corresponding slots 37a, 37b and 39a, 39b, respectively, located on interior walls of the housing 11. The pins 33a, 33b project transversely in both directions from the ends of their corresponding legs 31a, 31b that are opposite the calibration plate. The outwardly-projecting ends of these pins 33a, 33b are received within the slots 37a, 37b formed in the housing wall, and the inwardly-projecting ends of these pins 33a, 33b are received within slots 41a, 41b formed in the side of the sensor body 27. The pins 35a, 35b project outwardly from a mid-portion of their corresponding legs 31a, 31b, and they are received within the corresponding slots 39a, 39b formed in the housing wall. The slots 37a, 37b are arranged generally horizontally (i.e., parallel with the probe's longitudinal axis 23), and the slots 39a, 39b are arranged generally obliquely.

When the indexing handle 29 is manually retracted, the forward ends of the sensor body slots 41a, 41b eventually engage the inwardly-projecting ends of the pins 33a, 33b and urge them rearwardly. This causes the pins 35a, 35b to slide upwardly within the oblique slots 39a, 39b, which pivots the calibration plate 21 upwardly into alignment with the elongated probe's longitudinal axis 23. Eventually, the pins 33a, 33b reach the ends of the horizontal slots 37a, 37b, and the pins 35a, 35b reach the upper ends of the oblique slots 39a, 39b. Pivoting of the calibration plate therefore terminates.

Pivoting of the calibration plate 21 downwardly and away from the probe's longitudinal axis 23 occurs in an opposite fashion. In particular, forward movement of the indexing handle 29 and sensor body 27 allows the spring 30 to urge the calibration plate downwardly, while the pins 33a, 33b and 35a, 35b and respective slots 37a, 37b, and 39a, 39b guide the pivoting movement. The calibration plate is depicted in its inoperative position, out of alignment with the probe 15, in FIGS. 4 and 5.

A spring latch 101 mounted on the top side of the slidable sensor body 27 and a cooperating detent 103 located on the underside of the top wall of the housing 11 releasably hold the sensor body and probe 15 in their forward positions when a patient's temperature is being read. Similarly, a second spring latch 105 mounted on the sensor body's top side and a cooperating second detent 107 located on the underside of the housing's top wall releasably hold the sensor body and probe in their fully retracted positions. An electrical limit switch 109 mounted on the sensor body's top side, adjacent to the second spring latch, is automatically closed when the second spring latch engages the second detent, to signal the thermometer electronics that the calibration plate 21 is then positioned directly in front of the probe and that calibration of the thermometer may occur.

Figure 1:
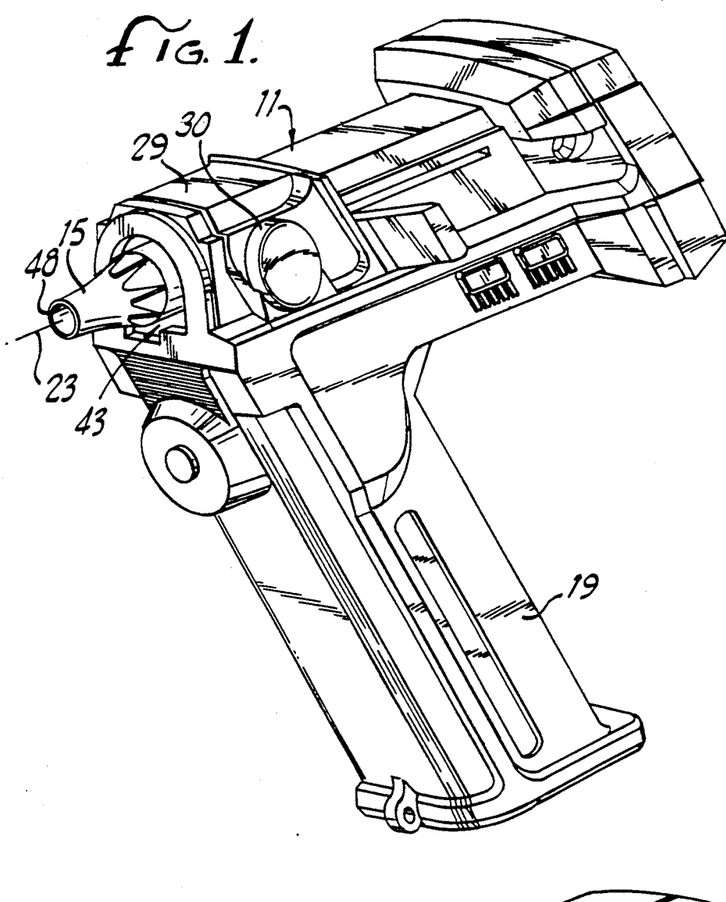
FIG. 1 is a perspective view of an infrared medical thermometer embodying the invention, shown with its elongated probe in its operative, extended position.
Figure 2:
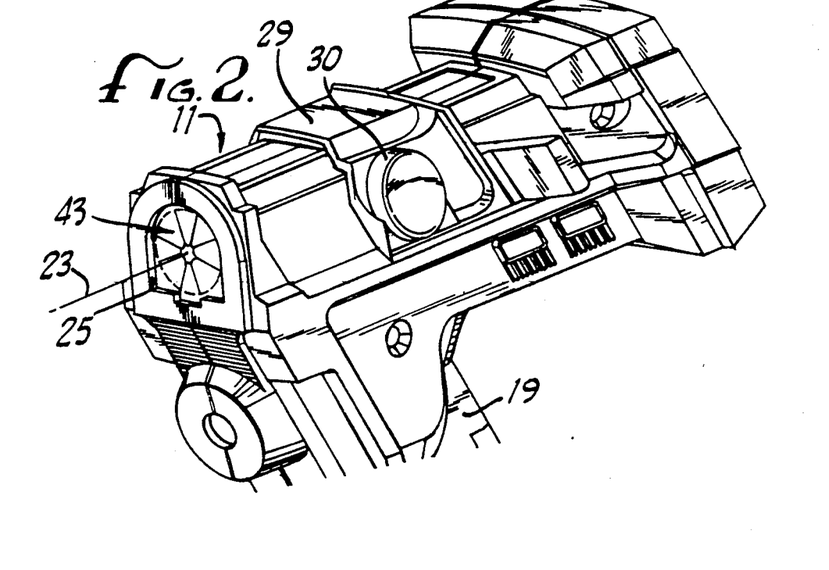
FIG. 2 is a fragmentary view of the front end of the thermometer of FIG. 1, shown with a protective probe cover positioned in alignment with the elongated probe's longitudinal axis as the probe is being advanced forwardly from its inoperative, retracted position toward its operative, extended position.

The infrared medical thermometer is intended for use in measuring the body temperatures of multiple patients. It therefore is important to place a hygienic protective probe cover 43 over the elongated probe 15 prior to its use with each patient. In one feature of the invention, such a multi-ply probe cover is automatically placed over the probe each time it advances from its retracted position (FIG. 3) through the opening 25 to its extended position (FIGS. 1 and 5). In addition, the thermometer is adapted to automatically remove and discard the probe cover after use, as the probe is retracted from its extended position to its retracted position.

More particularly, and with reference to FIGS. 3-5 and 7-8, it will be observed that a plurality of such protective probe covers 43 are connected end-to-end to form an elongated chain that is folded into a fan-folded configuration within a container 45 located within the handle portion 19 of the housing 11. The end-most cover is normally located at a forward end of the container, immediately below the opening 25 in the housing's front end. A pawl 47 is selectively engagable with this end-most cover, to advance the cover into alignment with the probe 15. Consequently, when the probe advances along its axis 23, from its retracted position (FIG. 3) to its extended position (FIG. 5), it projects through the protective probe cover and stretches a plastic film 48 of the cover completely over it.

The housing opening 25, through which the probe 15 extends, has a periphery shaped substantially the same as, but slightly smaller than, the periphery of the probe cover 43. The cover's plastic base layer therefore flexes slightly as it is forced through the opening by the advancing probe. As the probe cover is advanced through the opening, it is automatically detached from the trailing probe covers located within the container 45. When the probe is subsequently retracted into the housing 11, the opening's periphery functions to dislodge the slightly larger probe cover from the probe, whereby the cover can be easily discarded at that time. In addition, the tip of the probe is retracted far enough into the housing 11 to ensure that the probe cover is fully dislodged from the probe even if the probe cover's plastic film 48 sticks to the probe.

The mechanism for controlling movement of the pawl 47 includes a rack gear 49 secured to the underside of the sensor body 27 and movable with the indexing handle 29, a mating idler gear 51, and a driven gear 59. The driven gear 59 rotates on a common shaft with a bell crank 63. Advancing the indexing handle forwardly from the fully retracted position of FIG. 3 to the intermediate position of FIG. 4 moves the rack gear 49 forwardly, which rotates the idler gear 51 in a counterclockwise direction. The driven gear 59 and an inwardly-projecting nib 65 of the gear are thereby driven in a clockwise direction. The nib 65 engages a flexible arm 67 that is built into the bell crank, to rotate the bell crank clockwise and thus advance the pawl 47, which is connected to the bell crank's remote end.

Figure 4:
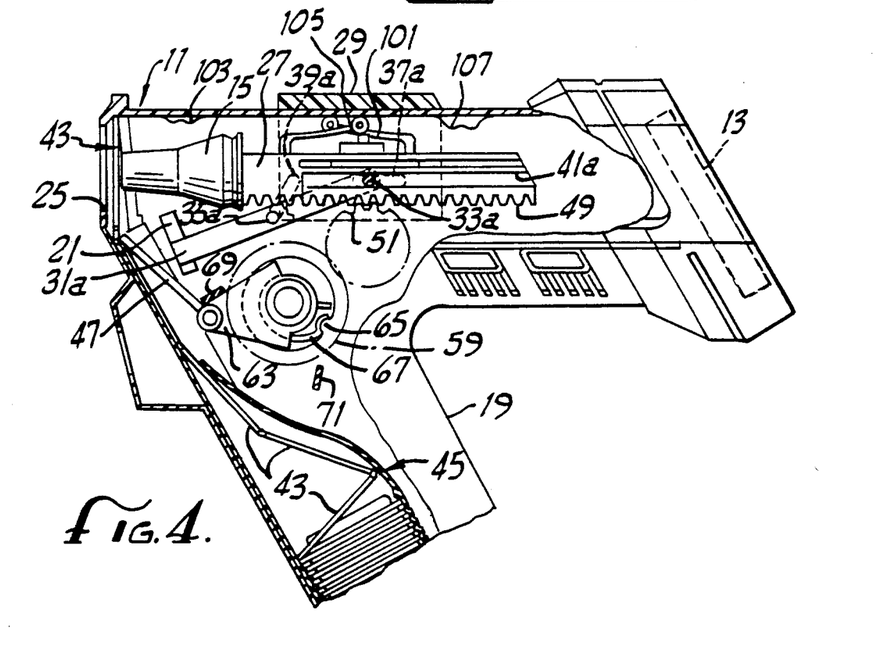
FIG. 4 is a side sectional view similar to FIG. 3, but showing the probe having been moved part way from its retracted position to its extended position, with the calibration reference pivoted away from the probe, and with the end-most protective cover positioned directly in front of the advancing probe.

When the bell crank 63 has been advanced to the intermediate position of FIG. 4, the end-most probe cover 43 will have reached a position directly in front of the advancing probe 15. Further movement of the pawl 47 and probe cover is mechanically inhibited by a stop 69 positioned to block the bell crank. Further clockwise rotation of the gear 59 causes the arm 67 to flex inwardly and allow the inwardly-projecting nib 65 to slide over it and continue advancing to the position depicted in FIG. 5. During this subsequent movement, the pawl remains in the same position.

After the patient's temperature has been measured, and it is desired for the thermometer to be reinitialized, the indexing handle 29 is manually moved rearwardly on the housing 11. This moves the rack gear 49 and sensor body 27 rearwardly, which rotates clockwise the idler gear 51 and, in turn, which rotates counterclockwise the driven gear 59 and inwardly-projecting nib 65. When the inwardly-projecting nib reaches the flexible arm 67, the arm and bell crank 63 are driven counterclockwise along with it. This returns the pawl 47 to the position of FIG. 3, where it engages the next succeeding probe cover 43. Further counterclockwise rotation of the bell crank is then mechanically inhibited by a stop 71, and the arm 67 flexes inwardly to allow the inwardly-projecting nib to ride over it and return to the position of FIG. 3. The structure is then in condition to begin moving the next succeeding probe cover into position to be stretched over the elongated probe 15.

Figure 8:
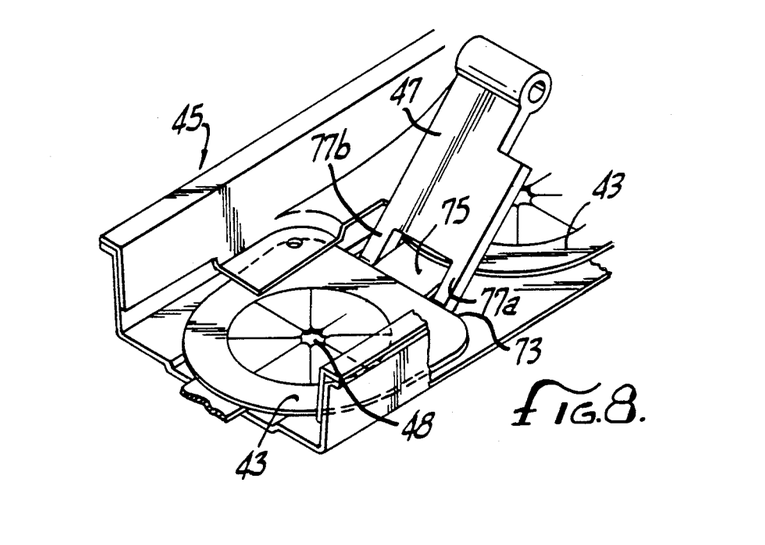
FIG. 8 is an enlarged detailed view of the pawl engaging the end-most protective probe cover, to advance it into a position in front of the elongated probe.
Figure 9:
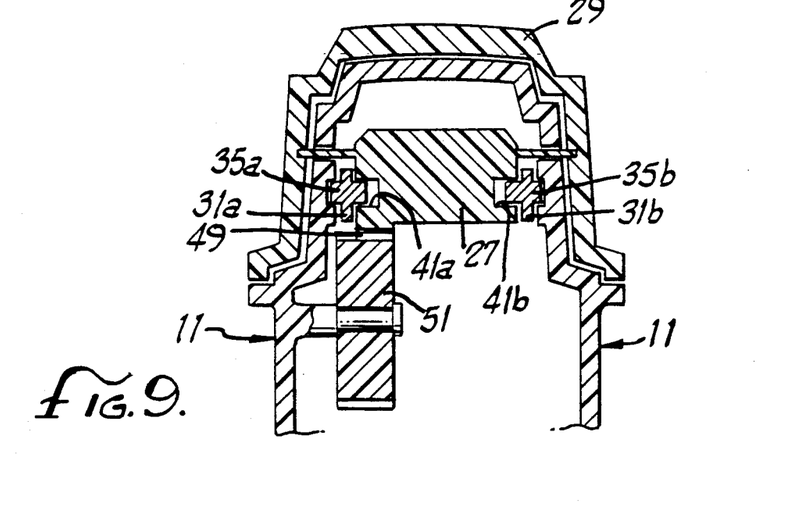
FIG. 9 is a fragmentary sectional view of the gearing mechanism for extending and retracting the probe, taken substantially in the direction of the arrows 9—9 in FIG. 3.

Engagement of the pawl 47 with the end-most protective probe cover 43 is best depicted in FIG. 8. In particular, it will be observed that the rear periphery 73 of the cover is generally straight, with rounded corners and with a thin strip 75 at its centerline for attaching it to the next-succeeding cover. The pawl is generally U-shaped, with two legs 77a and 77b for engaging the probe cover's rear periphery, on opposite sides of the center strip. This positive engagement ensures that forward movement of the pawl will push the probe cover into the desired position in front of the advancing probe 15, while pulling behind it the next-succeeding probe cover into the predetermined position where it can be engaged by the pawl during the next cycle. A slight spring bias provided by a coil spring (not shown) urges the pawl's operative end against the probe cover, to ensure that it fully engages the cover's rear periphery.

It should be appreciated from the foregoing description that the present invention provides an improved handheld infrared medical thermometer that is fully self-contained. An elongated probe is reciprocably movable between a retracted position, located fully within the thermometer housing, and an extended position, located exterior to the housing. In the extended position, the probe is adapted for insertion into a patient's outer ear canal. When the probe is retracted within the housing, a calibration reference plate is pivoted in front of the probe, to facilitate calibration. Advancement of the probe to its extended, operative position automatically pivots the reference plate away from the advancing probe and, in addition, automatically advances a disposable protective cover from a container for a large number of such covers into a position where it automatically stretches over the advancing probe to provide hygienic protection.

Although the invention has been described in detail with reference only to the preferred embodiment, those of ordinary skill in the art will appreciate that various modifications can be made without departing from the invention. Accordingly, the invention is defined only by the following claims.

We claim:

1. Infrared medical thermometer comprising:
   a housing adapted to be held in a user's hand;
   an elongated probe adapted to be inserted into a patient's ear canal to receive infrared radiation and provide a signal indicating the patient's body temperature;
   extension/retraction means for selectively extending the elongated probe to an operative position outside the housing when a patient's temperature is to be measured and for selectively retracting the elongated probe to an inoperative position fully within the housing when the measurement has been completed; and
   probe cover means for positioning a protective cover in alignment with the elongated probe while the probe is retracted within the housing such that, when the extension/retraction mean selectively extends the probe to its operative position, the protective cover is automatically placed over the probe.

2. Infrared thermometer apparatus as defined in claim 1, wherein:
   the protective cover includes a substantially flat base with a central aperture and further includes a stretchable plastic film extending across the aperture;
   the extension/retraction means is operable, while it extends the elongated probe to its operative position, to move the probe through the central aperture of the protective cover and stretch the plastic film over the probe; and
   the extension/retraction means is further operable, while it retracts the elongated probe to is inoperative position, to automatically remove the protective cover from the probe.

3. Infrared thermometer apparatus as defined in claim 1, wherein:
   the apparatus further includes a container carrying a plurality of substantially identical protective covers connected together end-to-end and
   the probe cover means includes a pawl for engaging the end-most protective cover and advancing it into alignment with the elongated probe while the probe is retracted within the housing.

4. Infrared thermometer apparatus as defined in claim 3, wherein:
   each adjacent pair of protective covers is connected together by a narrow strip aligned with the centers of the covers; and
   the pawl includes a U-shaped end adapted to engage the rearward edge of the end-most protective cover, on opposite sides of the narrow strip connecting the end-most cover with the adjacent cover, and thereby to urge the end-most cover into alignment with the elongated probe.

5. Infrared thermometer apparatus as defined in claim 1, and further including a calibration reference located within the housing and positioned directly in front of the elongated probe when the probe is retracted to its inoperative position fully within the housing.

6. Infrared thermometer apparatus as defined in claim 1, wherein:
   the elongated probe has a longitudinal axis;
   the extension/retraction means extends and retracts the elongated probe along its longitudinal axis;
   the apparatus further includes a calibration reference located within the housing and movable between an operative position directly in front of the elongated probe, when the probe is retracted to its inoperative position fully within the housing, and an inoperative position alongside the elongated probe, when the probe is extended to its operative position outside the housing; and
   the extension/retraction means includes means for selectively moving the calibration reference between its operative and inoperative positions.

7. Infrared thermometer apparatus as defined in claim 6, wherein the calibration reference includes:
   a plate adapted to be selectively positioned directly in front of the elongated probe;
   an arm secured to the plate; and
   a pin and cooperating slot carried by the arm and the housing, for guiding the plate and arm between the calibration reference's operative and inoperative positions.

8. Infrared thermometer apparatus as defined in claim 6, and further including:
   probe cover means for positioning a protective cover in alignment with the elongated probe while the probe is retracted within the housing such that, when the extension/retraction means selectively extends the probe to its operative position, the protective cover automatically covers the probe; and
   selectable actuator means for substantially simultaneously conditioning the calibration reference to move to its inoperative position, conditioning the probe cover means to position a protective cover in alignment with the elongated probe, and conditioning the extension/retraction means to extend the elongated probe to its operative position.

9. Infrared thermometer apparatus as defined in claim 8, wherein the selectable actuator means further includes means for substantially simultaneously conditioning the extension/retraction means to retract the elongated probe to its inoperative position, conditioning the probe cover means to engage a further protective cover, and conditioning the calibration reference to move to its operative position directly in front of the elongated probe.

10. A method for measuring a patient's body temperature, comprising steps of:
providing a housing adapted to be held in a user's hand and an associated elongated probe adapted to be inserted into a patient's ear canal to receive infrared radiation and provide a signal indicating the patient's body temperature;
selectively extending the elongated probe to an operative position outside the housing when a patient's temperature is to be measured;
selectively retracting the elongated probe to an inoperative position fully within the housing when the measurement has been completed; and
positioning a protective cover in alignment with the elongated probe while the probe is retracted within the housing such that, when the probe is extended to its operative position in the step of selectively extending, the protective cover is automatically placed over the probe.

11. A method as defined in claim 10, wherein:
the protective cover includes a substantially flat base with a central aperture and further includes a stretchable plastic film extending across the aperture;
the step of selectively extending includes a step of moving the probe through the central aperture of the protective cover, to stretch the plastic film over the probe; and
the step of selectively retracting includes a step of automatically removing the protective cover from the probe.

12. A method as defined in claim 10, wherein:
the method further includes a step of placing within the housing a container for a plurality of substantially identical protective covers connected together end-to-end to form an elongated chain; and
the step of selectively extending includes a step of engaging a pawl with the end-most protective cover and advancing the cover into alignment with the elongated probe while the probe is retracted within the housing.

13. A method as defined in claim 10, and further including a step of positioning a calibration reference within the housing, directly in front of the elongated probe when the probe is retracted to its inoperative position fully within the housing.

14. A method as defined in claim 10, and further including steps of:
providing a calibration reference within the housing;
selectively moving the calibration reference to a position directly in front of the elongated probe when the probe is retracted to its inoperative position fully within the housing; and
selectively moving the calibration reference to a position alongside the elongated probe when the probe is extended to its operative position outside the housing.

15. A method as defined in claim 14, wherein:
the method further includes a step of positioning a protective cover in alignment with the elongated probe while the probe is retracted within the housing such that, when the probe is extended to its operative position in the step of selectively extending the protective cover automatically covers the probe; and
the three steps of selectively moving the calibration reference to its position alongside the elongated probe positioning a protective cover in alignment with the elongated probe, and selectively extending the elongated probe, to its operative position all occur substantially simultaneously.

16. A method as defined in claim 15, wherein the steps of selectively retracting the elongated probe to its inoperative position and selectively moving the calibration reference to its position directly in front of the elongated probe both occur substantially simultaneously.

17. Infrared thermometer apparatus comprising:
a housing adapted to be held in a user's hand;
an elongated probe having a longitudinal axis and adapted to be inserted into a patient's ear to receive infrared radiation and provide a signal indicating the patient's body temperature;
extension/retraction means for selectively extending the elongated probe along its longitudinal axis to an operative position outside the housing when a patient's temperature is to be measured and for selectively retracting the elongated probe along its longitudinal axis to an inoperative position fully within the housing when the measurement has been completed;
a container located within the housing and carrying a plurality of substantially identical protective covers connected together end-to-end to form an elongated chain; wherein each protective cover includes a substantially flat base with a central aperture and further includes a stretchable plastic film extending across the aperture; and
wherein each adjacent pair of protective covers in the elongated chain is connected together by a narrow strip aligned with the centers of the covers;
probe cover means having a pawl with a U-shaped end adapted to engage the rearward edge of the end-most adjacent cover, to move the end-most cover into alignment protective cover in the elongated chain, on opposite sides of the narrow strip connecting the end-most cover with the with the elongated probe while the probe is retracted within the housing such that, when the extension/retraction means selectively extends the probe to its operative position, the protective cover automatically covers the probe;
wherein the extension/retraction means is operable, while it extends the elongated probe to its operative position, to move the probe through the central aperture of the protective cover and stretch the plastic film over the probe, and the extension/retraction means is further operable, while it retracts the elongated probe to its inoperative position, to automatically remove the protective cover from the probe;
a calibration reference located within the housing and movable between a position directly in front of the elongated probe when the probe is retracted to its inoperative position fully within the housing and a position alongside the elongated probe when the probe is extended to its operative position outside the housing; and selectable actuator means for substantially simultaneously conditioning the calibration reference to move to its position alongside the elongated probe, conditioning the probe cover means to position a protective cover in alignment with the elongated probe, and conditioning the extension/retraction means to extend the elongated probe to its operative position, wherein the selectable actuator means further includes means for substantially simultaneously conditioning the extension/retraction means to retract the elongated probe to its inoperative position, conditioning the pawl of the probe cover means to engage a further protective cover, and conditioning the calibration reference to move to its position directly in front of the elongated probe.

18. Infrared thermometer apparatus comprising:

a housing adapted to be held in a user's hand;

an elongated probe adapted to be inserted into a patient's ear canal to receive infrared radiation and provide a signal indicating to the patient's body temperature;

extension/retraction means for selectively extending the elongated probe to an operative position outside the housing when a patient's temperature is to be measured and for selectively retracting the elongated probe to an inoperative position fully within the housing when the measurement has been completed; and a calibration reference located within the housing and movable between an operative position directly in front of the probe, while the probe is retracted to its inoperative position fully within the housing, and an inoperative position alongside the probe, while the probe is extended to its operative position outside the housing.

19. Infrared thermometer apparatus as defined in claim 18, and further including probe cover means for positioning a protective cover in alignment with the elongated probe while the probe is retracted within the housing such that, when the extension/retraction means selectively extends the probe to its operative position, the protective cover is automatically placed over the probe.

20. Infrared thermometer apparatus as defined in claim 19, wherein:

the protective cover includes a substantially flat base with a central aperture and further includes a stretchable plastic film extending across the aperture;

the extension/retraction means is operable, while it extends the elongated probe to its operative position, to move the probe through the central aperture of the protective cover and stretch the plastic film over the probe; and the extension/retraction means is further operable, while it retracts the elongated probe to its inoperative position, to automatically remove the protective cover from the probe.

21. Infrared thermometer apparatus as defined in claim 19, wherein:

the apparatus further includes a container carrying a plurality of substantially identical protective covers connected together end-to-end; and the probe cover means includes a pawl for engaging the end-most protective cover and advancing it into alignment with the elongated probe while the probe is retracted within the housing.

22. Infrared thermometer apparatus as defined in claim 21, wherein:

each adjacent pair of protective covers in the elongated chain of covers is connected together by a narrow strip aligned with the centers of the covers; and the pawl includes a U-shaped end adapted to engage the rearward edge of the end-most protective cover, on opposite sides of the narrow strip connecting the end-most cover with the adjacent cover, and thereby to urge the end-most cover into alignment with the elongated probe.

23. Infrared thermometer apparatus as defined in claim 18, wherein:

the elongated probe has a longitudinal axis;

the extension/retraction means extends and retracts the elongated probe along its longitudinal axis; and the extension/retraction means includes means for selectively moving the calibration reference between its operative and inoperative positions.

24. Infrared thermometer apparatus as defined in claim 23, wherein the calibration reference includes:

a plate adapted to be selectively positioned directly in front of the elongated probe;

an arm secured to the plate; and a pin and cooperating slot carried by the arm and the housing, for guiding the plate and arm between the calibration reference's operative and inoperative positions.

25. Infrared thermometer apparatus as defined in claim 23, and further including:

probe cover means for positioning a protective cover in alignment with the elongated probe while the probe is retracted within the housing such that, when the extension/retraction means selectively extends the probe to its operative position the protective cover is automatically placed over the probe; and selectable actuator means for substantially simultaneously conditioning the calibration reference to move to its inoperative position, conditioning the probe cover means to position a protective cover in alignment with the elongated probe, and conditioning the extension/retraction means to extend the elongated probe to its operative position.

26. Infrared thermometer apparatus as defined in claim 25, wherein the selectable actuator means further includes means for substantially simultaneously conditioning the extension/retraction means to retract the elongated probe to its inoperative position, conditioning the probe cover means to engage a further protective cover, and conditioning the calibration reference to move to its operative position directly in front of the elongated probe.

27. A method for measuring a patient's body temperature, comprising steps of:

providing a housing adapted to be held in a user's hand and an associated elongated probe adapted to be inserted into a patient's ear canal to receive infrared radiation and provide a signal indicating the patient's body temperature;

selectively extending the elongated probe to an operative position outside the housing when a patient's temperature is to be measured;

selectively retracting the elongated probe to an inoperative position fully within the housing when the measurement has been completed;

providing a calibration reference within the housing;

selectively moving the calibration reference to a position directly in front of the elongated probe when the probe is retracted to its inoperative position fully within the housing; and selectively moving the calibration reference to a position alongside the elongated probe when the probe is extended to its operative position outside the housing.

28. A method as defined in claim 27, and further including a step of positioning a protective cover in alignment with the elongated probe while the probe is retracted within the housing such tat, when the probe is extended to its operative position in the step of selectively extending, the protective cover is automatically placed over the probe.

29. A method as defined in claim 28, wherein:

the protective cover includes a substantially flat base with a central aperture and further includes a stretchable plastic film extending across the aperture;

the step of selectively extending includes a step of moving the probe through the central aperture of the protective cover, to stretch the plastic film over the probe; and the step of selectively retracting includes a step of automatically removing the protective cover from the probe.

30. A method as defined in claim 28, wherein:

the method further includes a step of placing within the housing a container for a plurality of substantially identical protective covers connected together end-to-end to form an elongated chain; and the step of selectively extending includes a step of engaging a pawl with the end-most protective cover and advancing the cover into alignment with the elongated probe while the probe is retracted within the housing.

31. A method as defined in claim 27, wherein:

the method further includes a step of positioning a protective cover in alignment with the elongated probe while the probe is retracted within the housing such that, when the probe is extended to its operative position in the step of selectively extending, the protective cover is automatically placed over the probe; and the three steps of selectively moving the calibration reference to its position alongside the elongated probe, positioning a protective cover in alignment with the elongated probe, and selectively extending the elongated probe to its operative position all occur substantially simultaneously.

32. A method as defined in claim 31, wherein the steps of selectively retracting the elongated probe to its inoperative position and selectively moving the calibration reference to its position directly in front of the elongated probe both occur substantially simultaneously.

* * * * *

UNITED STATES PATENT AND TRADEMARK OFFICE
CERTIFICATE OF CORRECTION

PATENT NO. : 4,993,424

DATED : February 19, 1991

INVENTOR(S) : Edward D. Suszynski et al.

It is certified that error appears in the above-identified patent and that said Letters Patent is hereby corrected as shown below:

Col. 7, line 54: change "mean" to -- means --;

Col. 10, lines 47-48: delete "adjacent cover to move the end-most cover into alignment";

Col. 10, line 50: delete "cover with the with the" and insert -- cover with the adjacent cover, to move the end-most cover into alignment with the --;

Col. 11, line 24: delete "to";

Col. 12, line 40: after the word "position" insert -- , --; and

Col. 13, line 16: "such tat" should read -- such that --.

Signed and Sealed this

Fourteenth Day of July, 1992

Attest:

DOUGLAS B. COMER

*Attesting Officer*     *Acting Commissioner of Patents and Trademarks*